(12) United States Patent
Lindemann et al.

(10) Patent No.: US 7,998,179 B2
(45) Date of Patent: *Aug. 16, 2011

(54) FLEXIBLE BONE PLATES AND METHODS FOR DYNAMIC SPINAL STABILIZATION

(75) Inventors: Gary S. Lindemann, Collierville, TN (US); Brian R. Harris, Cordova, TN (US); Jason Michael May, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/592,511

(22) Filed: Nov. 25, 2009

(65) Prior Publication Data

US 2010/0076495 A1   Mar. 25, 2010

Related U.S. Application Data

(62) Division of application No. 11/370,700, filed on Mar. 8, 2006, now Pat. No. 7,641,675.

(51) Int. Cl.
*A61B 17/66* (2006.01)

(52) U.S. Cl. .......................................... 606/282; 606/71

(58) Field of Classification Search .......... 606/280–299, 606/70, 71, 915
See application file for complete search history.

(56) References Cited

U.S. PATENT DOCUMENTS

| | | | |
|---|---|---|---|
| 5,616,142 A | 4/1997 | Yuan et al. | |
| 5,672,177 A | 9/1997 | Seldin | |
| 5,827,286 A * | 10/1998 | Incavo et al. | 606/71 |
| 6,306,136 B1 | 10/2001 | Baccelli | |
| 6,402,756 B1 | 6/2002 | Ralph et al. | |
| 6,666,867 B2 | 12/2003 | Ralph et al. | |
| 6,689,134 B2 | 2/2004 | Ralph et al. | |
| 6,852,113 B2 | 2/2005 | Nathanson et al. | |
| 6,932,820 B2 | 8/2005 | Osman | |
| 7,318,825 B2 * | 1/2008 | Butler et al. | 606/71 |
| 7,635,364 B2 * | 12/2009 | Barrall et al. | 606/70 |
| 7,763,056 B2 * | 7/2010 | Dalton | 606/282 |
| 2002/0183754 A1 | 12/2002 | Michelson | |
| 2002/0183755 A1 | 12/2002 | Michelson | |
| 2002/0183756 A1 | 12/2002 | Michelson | |
| 2002/0183757 A1 | 12/2002 | Michelson | |
| 2003/0060828 A1 | 3/2003 | Michelson | |
| 2003/0114856 A1 * | 6/2003 | Nathanson et al. | 606/70 |
| 2003/0130661 A1 | 7/2003 | Osman | |
| 2004/0019353 A1 | 1/2004 | Freid et al. | |
| 2004/0049279 A1 * | 3/2004 | Sevrain | 623/17.13 |
| 2004/0158250 A1 | 8/2004 | Chappuis | |
| 2004/0167521 A1 | 8/2004 | De Windt | |
| 2004/0181229 A1 | 9/2004 | Michelson | |
| 2004/0186476 A1 | 9/2004 | Michelson | |
| 2004/0204712 A1 | 10/2004 | Kolb et al. | |
| 2004/0204713 A1 | 10/2004 | Abdou | |
| 2004/0215195 A1 | 10/2004 | Shipp et al. | |
| 2005/0010227 A1 | 1/2005 | Paul | |
| 2005/0027297 A1 | 2/2005 | Michelson | |
| 2005/0027298 A1 | 2/2005 | Michelson | |
| 2005/0043732 A1 | 2/2005 | Dalton | |

(Continued)

*Primary Examiner* — Eduardo C Robert
*Assistant Examiner* — Jan Christopher Merene

(57) ABSTRACT

A plating system and method include a bone plate with at least a first vertebral engaging portion and a second vertebral engaging portion connected by flexible intermediate portions to permit translation of the vertebrae to which the bone plate is attached. The bone plate may further include a guide assembly extending between the vertebral engaging portions that permits at least uni-directional translation while enhancing resistance of the bone plate to bending forces.

20 Claims, 10 Drawing Sheets

U.S. PATENT DOCUMENTS

| | | |
|---|---|---|
| 2005/0085812 A1 | 4/2005 | Sherman et al. |
| 2005/0085816 A1 | 4/2005 | Michelson |
| 2005/0137597 A1 | 6/2005 | Butler et al. |
| 2005/0149026 A1 | 7/2005 | Butler et al. |
| 2005/0177160 A1 | 8/2005 | Baynham et al. |
| 2005/0192576 A1 | 9/2005 | Michelson |
| 2005/0216009 A1 | 9/2005 | Michelson |
| 2005/0216010 A1 | 9/2005 | Michelson |
| 2005/0216011 A1 | 9/2005 | Paul |
| 2006/0116683 A1 | 6/2006 | Barrall et al. |
| 2006/0235398 A1* | 10/2006 | Farris et al. ............... 606/69 |
| 2006/0235405 A1 | 10/2006 | Hawkes |
| 2007/0213729 A1 | 9/2007 | Lindemann et al. |
| 2007/0293864 A1 | 12/2007 | Reimels et al. |
| 2008/0147125 A1* | 6/2008 | Colleran et al. ............ 606/280 |
| 2008/0154312 A1* | 6/2008 | Colleran et al. ............ 606/283 |
| 2008/0215097 A1 | 9/2008 | Ensign et al. |

* cited by examiner

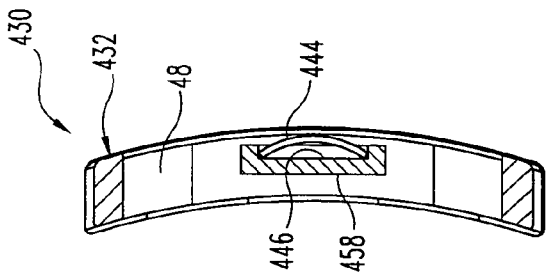
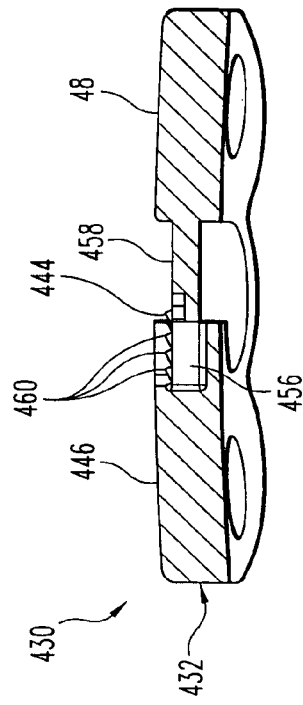
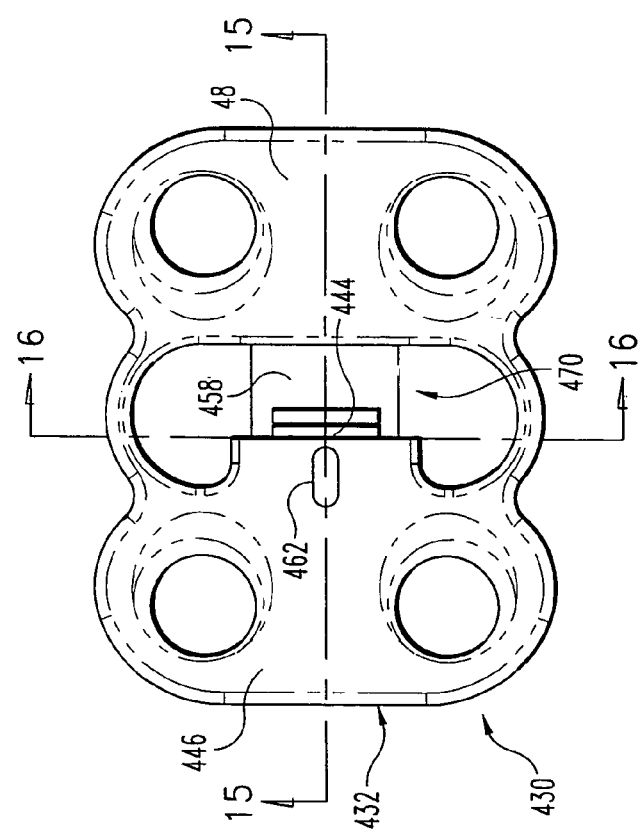

FLEXIBLE BONE PLATES AND METHODS FOR DYNAMIC SPINAL STABILIZATION

CROSS REFERENCE TO RELATED APPLICATION

The present application is a divisional application of U.S. Patent application Ser. No. 11/370,700 filed on Mar. 8, 2006, and now U.S. Pat. No. 7,641,675, which is hereby incorporated by reference in its entirety.

BACKGROUND

Bone plates can be engaged to adjacent bony portions of a bone or of a bony segment to stabilize the bony portions. Anchors or fasteners, such as bone screws, can be used to engage bone plates to the bony portions. In spinal surgical procedures, it can be desirable to provide stress on an interbody implant positioned between vertebrae to promote bone growth and fusion of adjacent vertebrae. Plates that rigidly maintain the separation distance between vertebrae can shield bone graft from stress and can result in less than optimal bone growth and fusion of the vertebrae.

There remains a need for devices and methods that can be employed efficiently and effectively for stabilizing one or more levels of a spinal column while preventing stress shielding of bone graft positioned to fuse the one or more levels.

SUMMARY

There is provided a spinal plating system with a plate body that can flex or deform in response to compression loading of the spinal column to maintain loading on bone graft in a disc space between vertebrae to which the plate is engaged. The plate can include a guide assembly that has a guide member movably received in a receptacle at least in response to compression loading. The guide assembly can provide resistance to bending forces exerted on the plate as a result of extension and flexion of the spinal column.

According to another aspect, a spinal plating system includes a plate body extending along a longitudinal axis between a first end and an opposite second end. The plate body has a length along the longitudinal axis sized to extend between at least a first vertebra and a second vertebra of the spinal column. The plate body includes first and second vertebral engaging portions each with at least one hole extending between an upper surface and a lower surface of the plate body to receive an anchor to secure the vertebral engaging portions to respective ones of the first and second vertebrae. The plate body also includes first and second intermediate portions extending between the first and second vertebral engaging portions along opposite sides of the plate body. The first and second intermediate portions and the first and second vertebral engaging portions define a window therebetween. The first and second intermediate portions are structured to flex and permit the first and second vertebral engaging portions to move toward one another along the longitudinal axis in response to compression loading along the longitudinal axis. The plating system also includes a guide assembly in the window along the longitudinal axis extending between and engaged to the first and second vertebral engaging portions. The guide assembly includes a guide member movably received in a receptacle as the first and second vertebral engaging portions move toward one another.

According to another aspect, a spinal plating system includes a plate body extending along a longitudinal axis between a first end and an opposite second end. The plate body has a length along the longitudinal axis sized to extend between at least first and second vertebrae of the spinal column. The plate body includes first and second vertebral engaging portions each with at least one hole extending between an upper surface and a lower surface of the plate body to receive an anchor to secure the first and second vertebral engaging portions to respective ones of first and second vertebrae. The plating system also includes a retaining element adjacent the upper surface associated with at least one of the plate holes. The retaining element includes a number of resilient fingers circumferentially positioned about the at least one hole. The fingers are separated from one another by a groove and each finger includes a first leg extending proximally from the plate body and a second leg at an end of the first leg extends radially inwardly toward the other fingers.

According to another aspect, a spinal plating system includes a plate body extending along a longitudinal axis between a first end and an opposite second end. The plate body has a length along the longitudinal axis sized to extend between at least a first vertebra and a second vertebra of the spinal column. The plate body includes first and second vertebral engaging portions each with at least one hole extending between an upper surface and a lower surface of the plate body. The at least one holes each receive an anchor to secure the respective first and second vertebral engaging portions to respective ones of the first and second vertebrae. The plating system also includes at least one intermediate portion extending between the first and second vertebral engaging portions having opposite ends integrally fixed with respective ones of the first and second vertebral engaging portions to form a unitary structure. The at least one intermediate portion is structured to deform and permit the first and second vertebral engaging portions to move toward one another along the longitudinal axis in response to compression loading along the longitudinal axis. The plating system also includes a guide assembly extending between and engaged to the first and second vertebral engaging portions. The guide assembly includes a guide member movably received in a receptacle as the first and second vertebral engaging portions move toward one another.

In yet another aspect, a method for stabilizing at least one level of a spinal column comprises: engaging a first vertebral engaging portion of a spinal plate to a first vertebra with at least one anchor extending through the first vertebral engaging portion; engaging a second vertebral engaging portion of the spinal plate to a second vertebra with at least one anchor extending through the second vertebral engaging portion, wherein the spinal plate includes a longitudinal axis extending along the first and second vertebrae when engaged to the first and second vertebrae; and compressing the first and second vertebrae to flex at least one intermediate portion extending between the first and second vertebral engaging portions, the intermediate portion lying in a plane in which the first and second vertebral engaging portions lie and being structured to flex in the plane transversely to the longitudinal axis to permit movement of the first and second vertebrae toward one another.

These and other aspects are discussed further below.

BRIEF DESCRIPTION OF THE FIGURES

FIG. 14 is a top plan view of another embodiment spinal plate.

FIG. 15 is a section view along line 15-15 of FIG. 14.

FIG. 16 is a section view along line 16-16 of FIG. 14.

DESCRIPTION OF THE ILLUSTRATED EMBODIMENTS

Figure 1:
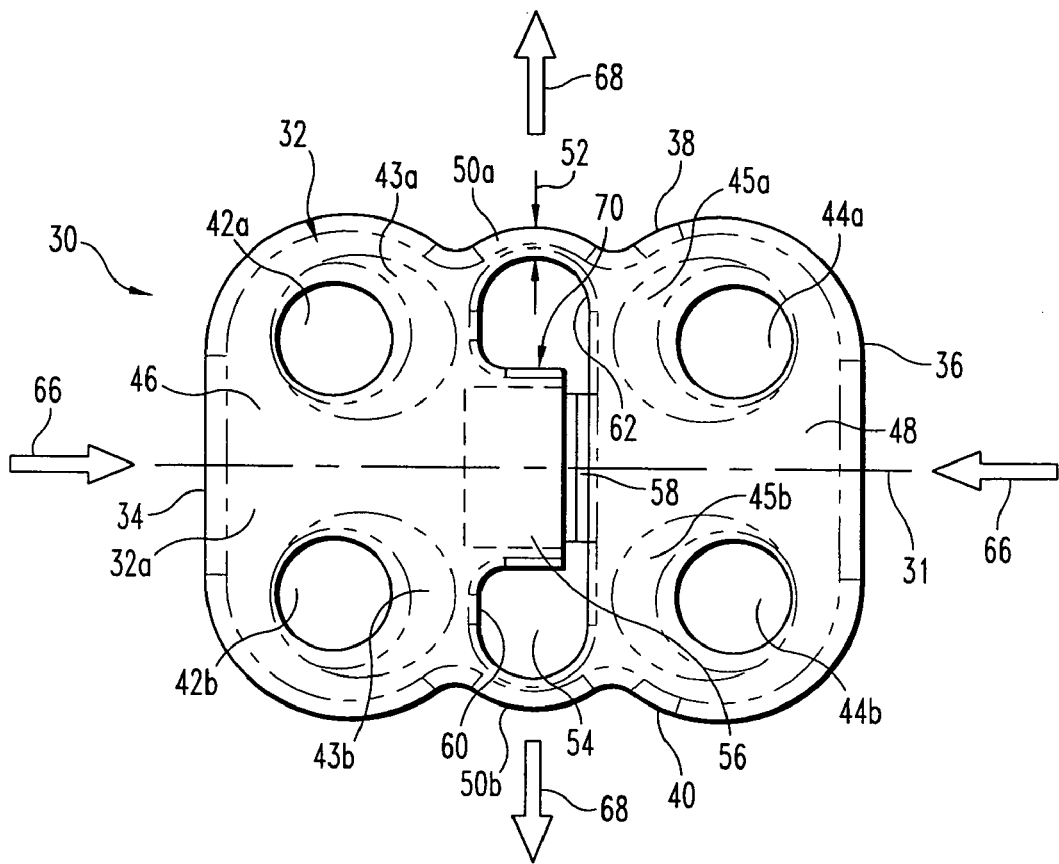
FIG. 1 is a top plan view of one embodiment spinal plate.

For the purposes of promoting an understanding of the principles of the invention, reference will now be made to the embodiments illustrated in the drawings and specific language will be used to describe the same. It will nevertheless be understood that no limitation of the scope of the invention is hereby intended, such alterations and further modifications in the illustrated devices, and such further applications of the principles of the invention as illustrated herein being contemplated as would normally occur to one skilled in the art to which the invention relates.

Bone plates are engageable along two or more vertebrae of a spinal column to stabilize one or more levels of the spinal column. Such stabilization can be employed, for example, to maintain or control a desired relative positioning between the vertebrae during fusion. The bone plates can be engaged to the vertebrae with bone anchors, and may include one or more retaining elements associated with one or more of the fasteners to prevent the fasteners from backing out relative to the plate. The bone plates include at least one intermediate portion extending between first and second vertebral engaging portions. The at least one intermediate portion can bend and flex in response to loading applied to the plate to allow movement of the vertebral engaging portion, and thus the vertebrae engaged thereto, toward and away from one another. The bone plates can also include a guide assembly extending between the vertebral engaging portions to provide strength to the bone plate to resist bending forces applied to the bone plate resulting from flexion and extension of the vertebral levels while allowing movement of the vertebral engaging portions relative to one another as result of at least compression forces.

Referring now to FIG. 1 there is shown a spinal plate 30 having a plate-like body 32 extending along a longitudinal axis 31 between a first end 34 and an opposite second end 36 with a length sized to extend between vertebrae of at least one vertebral level. Plate 32 includes an upper or proximal surface 32a and an opposite distal lower surface that is positionable along the vertebrae. The lower surface can be curved about and/or along longitudinal axis 31 to conform to the profile of the adjacent vertebrae. Sidewalls 38, 40 extend along opposite sides of body 32 between first and second ends 34, 36.

Body 32 includes a first vertebral engaging portion 46 adjacent first end 34 and a second vertebral engaging portion 48 adjacent second end 36. Body 32 also includes a pair of holes 42a, 42b adjacent first end 34 in first vertebral engaging portion 46, and a second pair of holes 44a, 44b adjacent second end 36 in second vertebral engaging portion 48. Holes 42a, 42b and holes 44a, 44b are located on opposite sides of longitudinal axis 31, and are configured to receive a bone anchor, such as a bone screw, to secure plate 30 to a vertebral body underlying plate 30 at the respective vertebral engaging portions 46, 48. Other embodiments contemplate that plate 30 can be provided with a single hole in one or both of the vertebral engaging portions 46, 48, or with more than two holes in one or both of the vertebral engaging portions 46, 48. Holes 42a, 42b, 44a, 44b can include spherically-shaped recessed portions 43a, 43b, 45a, 45b, respectively, adjacent upper surface 32a to allow the bone anchors to recess into plate 30 and reduce the profile of the assembly when attached along the spinal column.

First vertebral engaging portion 46 and second vertebral engaging portion 48 can be connected with one another via flexible or deformable intermediate portions 50a, 50b extending therebetween. Intermediate portions 50a, 50b each have a width 52 transverse to longitudinal axis 31 that is substantially smaller than a width of window 54 between intermediate portions 50a, 50b. The ends of intermediate portions 50a, 50b can be integrally formed with and immovably fixed to the respective adjacent vertebral engaging portion 46, 48 to form a unitary structure. Intermediate portions 50a, 50b are located along respective ones of the sidewalls 38, 40 of plate body 32. A window 54 extends through body 32 between intermediate portions 50a, 50b and between vertebral engaging portions 46, 48. Intermediate portions 50a, 50b can be convexly curved away from longitudinal axis 31 to form a bowed or arcuate shape. When plate 30 is positioned anteriorly along vertebrae, intermediate portions 52a, 52b are bowed laterally outwardly.

The ends of intermediate portions 50a, 50b can be immovably fixed to vertebral engaging portions 46, 48. Intermediate portions 50a, 50b can be integrally and unitarily formed with vertebral engaging portions 46, 48 to provide a one-piece plate body 32 that can flex or deform in response to compressive loads 66. In particular, the bowed or arcuate shape and relatively small width of intermediate portions 50a, 50b allow flexing or deforming of intermediate portions 50a, 50b laterally outwardly away from longitudinal axis 31, as indicated by arrows 68. The deformation or bowing of intermediate portions 50a, 50b occurs in the same plane in which vertebral engaging portions 46, 48 lie, and therefore intermediate portion 50a, 50b do not impinge on the disc space or the tissue along upper surface 32a of plate 30 when it is engaged to the spinal column. In addition, first and second vertebral engaging portions 46, 48 can move toward and away from one another without sliding movement of two or more portions of the plate body relative to one another.

First vertebral engaging portion 46 includes a first transverse wall 60 extending along one side of window 54 and second vertebral engaging portion 48 includes a second transverse wall 62 extending along the other side of window 54. As body 32 of plate 30 is axially compressed along longitudinal axis 31, transverse walls 60, 62 move toward one another reducing the height of window 54. In addition, as body 32 of plate 30 is axially tensioned, transverse walls 60, 62 move away from one another thereby enlarging window 54.

Body 32 can be subject to bending moments as the vertebrae to which plate 30 is attached move toward and away from one another during spinal extension and flexion. Spinal plate 30 can include a guide assembly 70 between vertebral engaging portions 46, 48 that guide movement of vertebral engaging portion portions 46, 48 relative to one another as plate 30 flexes and also to provide cross-sectional area to resist bending forces created by spinal extension and flexion motion.

Guide assembly 70 can include a guide member 58 that is axially received in and movable relative to a guide receptacle 56. In the illustrated embodiment, guide member 58 extends axially along axis 31 from second transverse wall 62 toward first vertebral engaging portion 46, and receptacle 56 extends along axis 31 from first transverse wall 60 toward second vertebral engaging portion 48. Guide member 58 is axially received in an opening into receptacle 56 and guided in receptacle 56 as first and second vertebral engaging portions 46, 48 move toward and away from one another. Guide member 58 can include a rectangular shape that is received through a complementary-shaped opening of receptacle 56 into a similarly shaped cavity defined by receptacle 56 to limit rotational or twisting movement between vertebral engaging portions 46, 48.

Other embodiments contemplate that guide member 58 can extend from first vertebral engaging portion 46, and receptacle 56 can extend from second vertebral engaging portion 48. Guide member 58 and receptacle 56 can be separate components, and body 32 of plate 30 can be molded around guide member 58 and receptacle 56. In another embodiment, guide member 58 and receptacle 56 are attached with body 32 after formation of body 32.

Figure 2:
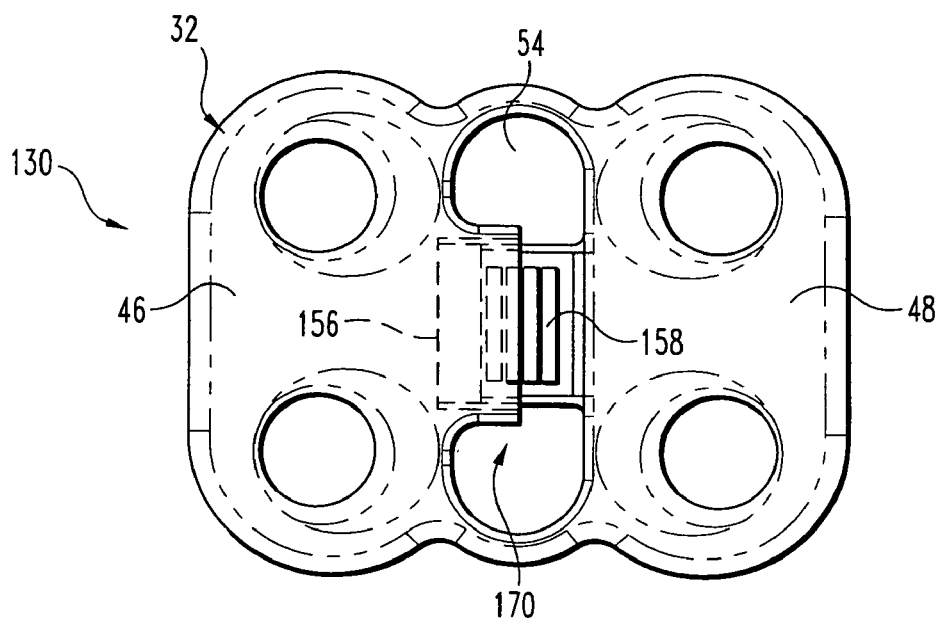
FIG. 2 is a top plan view of another embodiment spinal plate.

In FIG. 2 there is shown another embodiment plate 130 that is substantially like plate 30 discussed above, and like elements are designated with the same reference numerals. Spinal plate 130 includes another embodiment guide assembly 170. Guide assembly 170 includes a guide member 158 and a receptacle 156 for receiving guide member 158. Guide assembly 170 differs from guide assembly 70 in that receptacle 156 and guide member 158 have a ratcheting configuration that permits uni-directional translation while resisting translation in the opposite direction.

Figure 3:
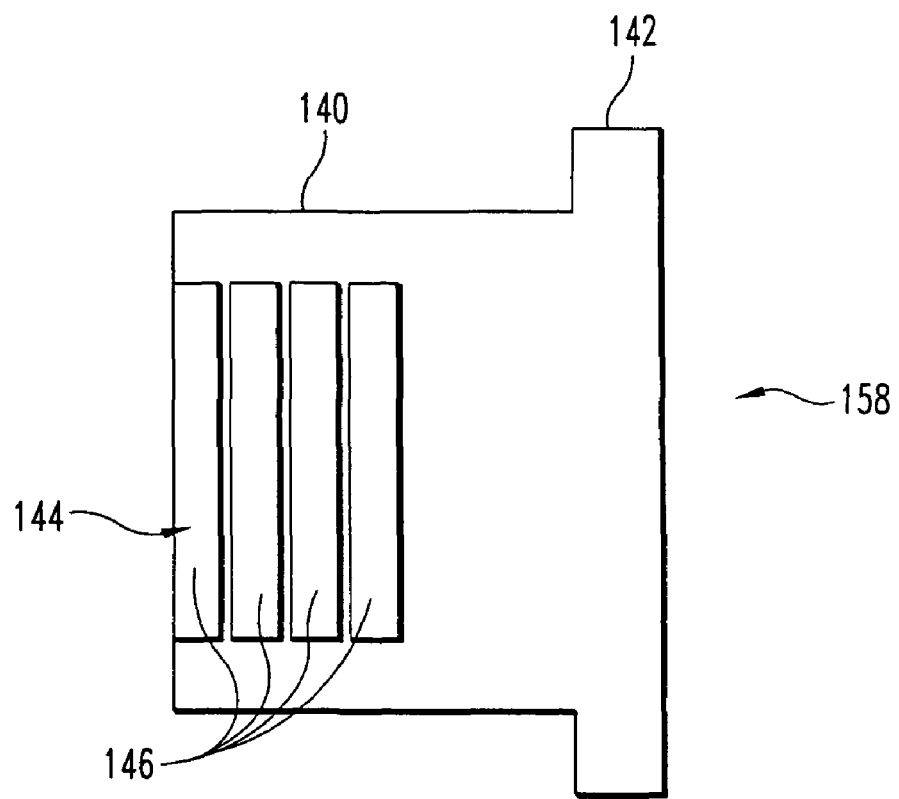
FIG. 3 is a top plan view of a guide member comprising a portion of the spinal plate of FIG. 2.
Figure 4:
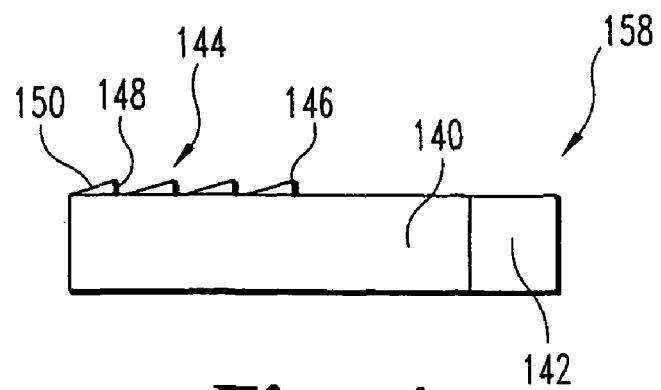
FIG. 4 is an elevational view of the guide member of FIG. 3.
Figure 5:
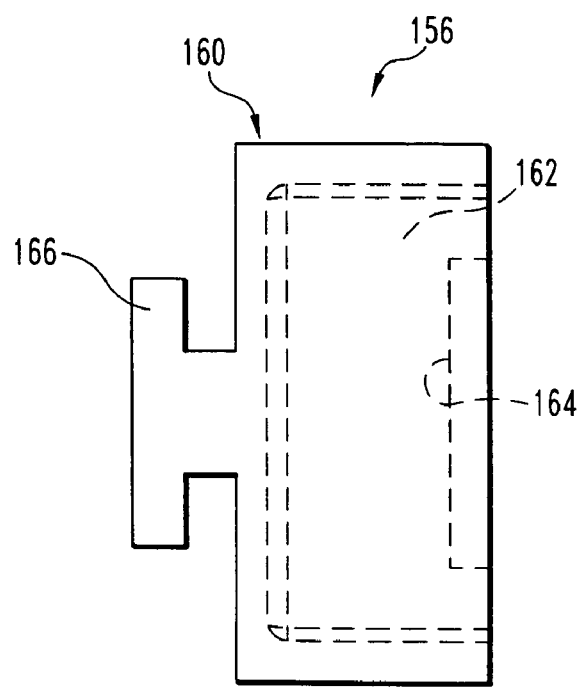
FIG. 5 is a top plan view of a receptacle of the spinal plate of FIG. 2.
Figure 6:
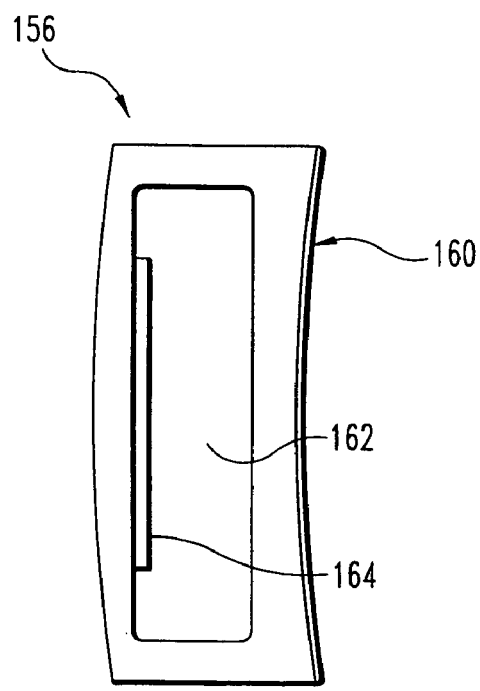
FIG. 6 is an end elevational view of the receptacle of FIG. 5.

FIGS. 3-4 show guide member 158 in isolation and FIGS. 5-6 show receptacle 156 in isolation. Guide member 158 includes a body portion 140 having a retaining arm 142 at one end thereof. Retaining arm 142 can facilitate molding or attachment of plate body 32 around or to guide member 158. Body portion 140 also includes a toothed surface portion 144 along a surface thereof. Toothed surface portion 144 includes a number teeth 146 projecting therefrom. Teeth 146 each include a vertically oriented wall portion 148 and a sloped wall portion 150. As shown in FIG. 2, guide member 158 can be engaged with one of the vertebral engaging portions 46, 48 and extend axially therefrom toward the other vertebral engaging portion 46, 48.

Receptacle 156 includes a body 160 that defines a cavity 162 sized and shaped to receive body portion 140 of guide member 156 as shown in FIG. 2. An end of body 160 opposite the opening of cavity 162 includes a retaining arm 166 that facilitates molding or attachment of receptacle 156 to plate body 32. Body 160 also includes a retaining lip 164 extending into cavity 162.

When guide member 158 and receptacle 156 are assembled with body 32 of plate 130, retaining lip 164 is positionable in contact with toothed surface portion 144 and engageable with an aligned one of the teeth 146 of toothed surface portion 144. Retaining lip 164 can include a vertically oriented wall portion 168 that abutting engages vertically oriented wall portion 148 of the engaged tooth 146 to prevent vertebral engaging portions 46, 48 from moving away from one another. As compression loads are applied to vertebral engaging portions 46, 48, retaining lip 164 can slide along sloped surface 150 of the next adjacent tooth 146 until wall portion 168 is aligned with the vertically oriented wall portion 148 of the next adjacent tooth 146.

Figure 7:
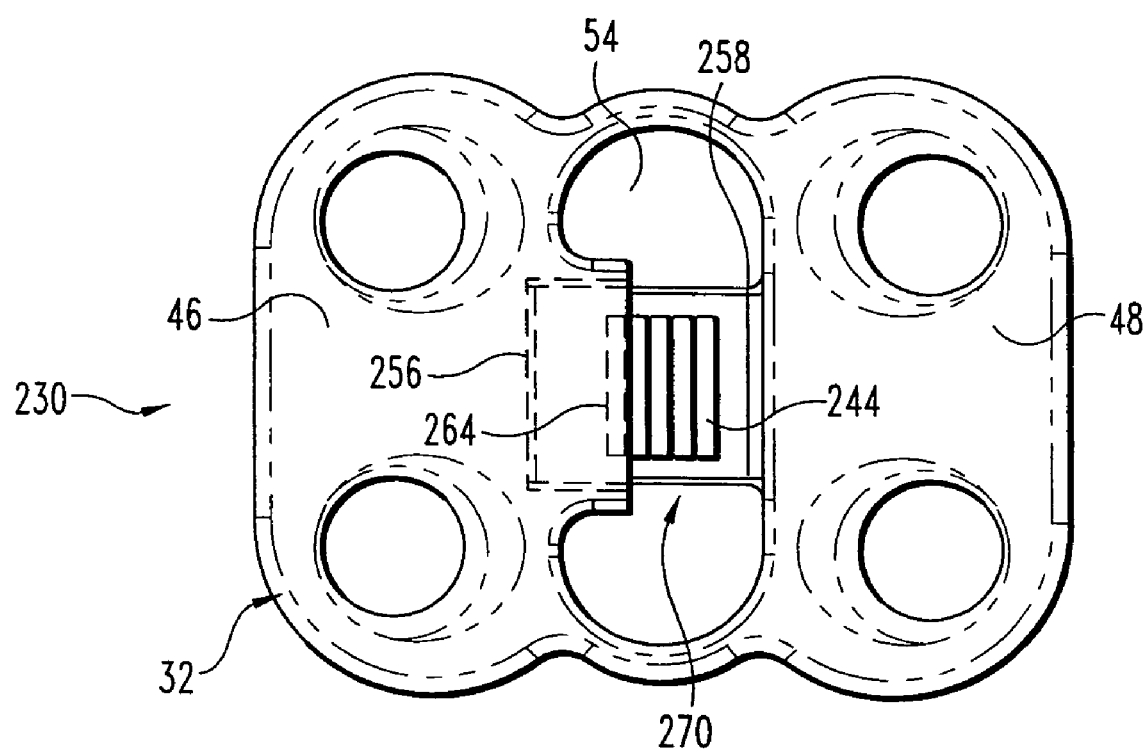
FIG. 7 is a top plan view of another embodiment spinal plate.

Referring now to FIG. 7, there is shown another embodiment plate 230 that can be substantially identical to plate 30 discussed above, and like elements are designated with like reference numerals. However, plate 230 includes another embodiment guide assembly 270 that has a guide member 258 extending axially from one of the vertebral engaging portions 46, 48 and a receptacle 256 extending axially from the other of the vertebral engaging portions 46, 48 and positioned to receive guide member 258. Unlike guide assembly 170 discussed above, guide member 258 is sized relative to window 54 and receptacle 256 so that when plate 230 is in its normal, uncompressed state, guide member 258 is not received in receptacle 256. Accordingly, guide member 258 and/or receptacle 256 can be formed integrally with body 32 to provide a spinal plate 230 having a unitary, one-piece construction of guide assembly 270 and plate body 32.

Guide member 258 can include a toothed surface 244 like guide member 158 discussed above, and receptacle 256 can including a retaining lip 264 oriented toward the toothed surface 244. When plate 230 is attached to the spinal column, it can flex in response to compression and tension loads with resistance provided by plate body 32 but not guide assembly 270. When the compression forces are great enough, body 32 can flex sufficiently to position guide member 258 in receptacle 256 with the retaining lip 264 engaged to the toothed surface 244. In this configuration, translation is uni-directionally controlled and movement of the vertebrae away from one another is limited by guide assembly 270 in addition to body 32.

Figure 8:
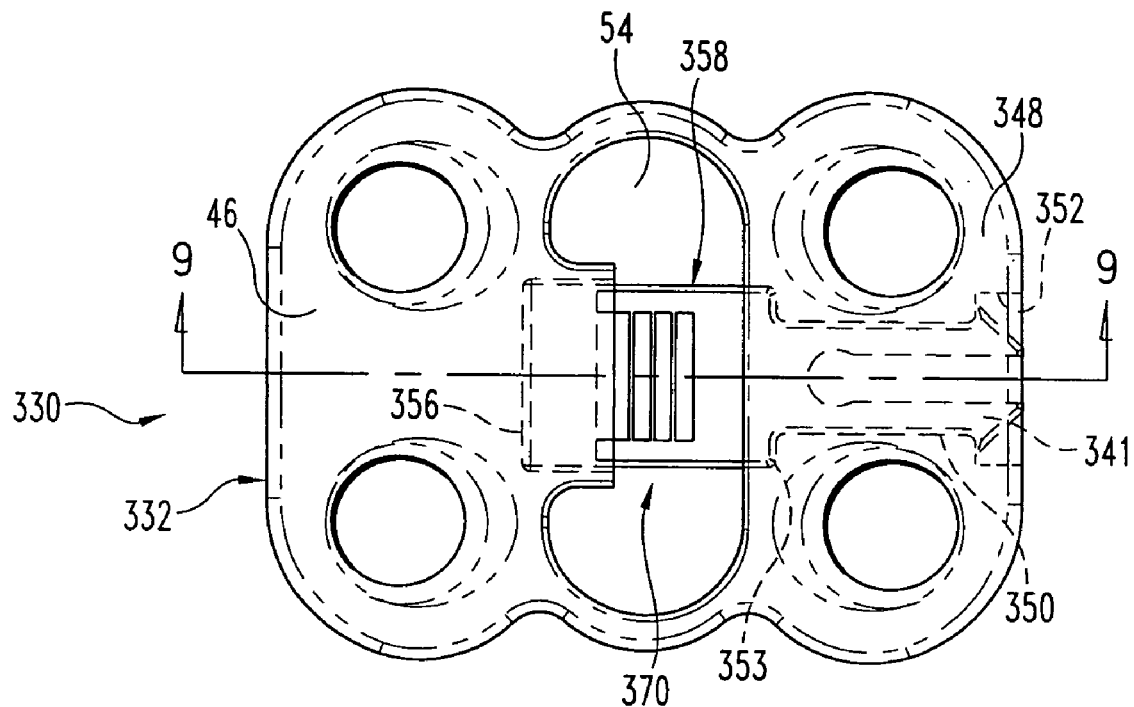
FIG. 8 is a top plan view of another embodiment spinal plate.
Figure 9:
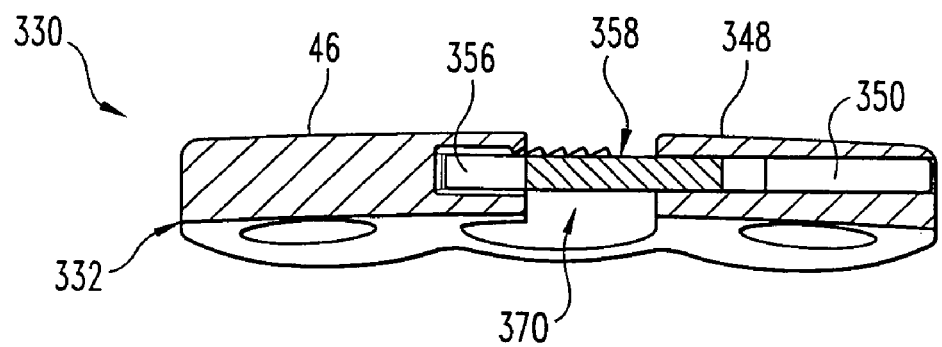
FIG. 9 is a section view along line 9-9 of FIG. 8.

Referring now to FIGS. 8-9, there is shown a spinal plate 330 that includes a plate body 332 that is similar to plate body 32 discussed above and like elements are designated with like reference numerals. Body 332 differs from body 32 in that it includes a vertebral engaging portion 348 defining an internal and axially extending guide member retaining passage 350. Spinal plate 330 also includes another embodiment guide assembly 370 with a guide member 358 removably engageable in retaining passage 350, and vertebral engaging portion 48 includes a receptacle 356 for receiving guide member 358.

Figure 12:
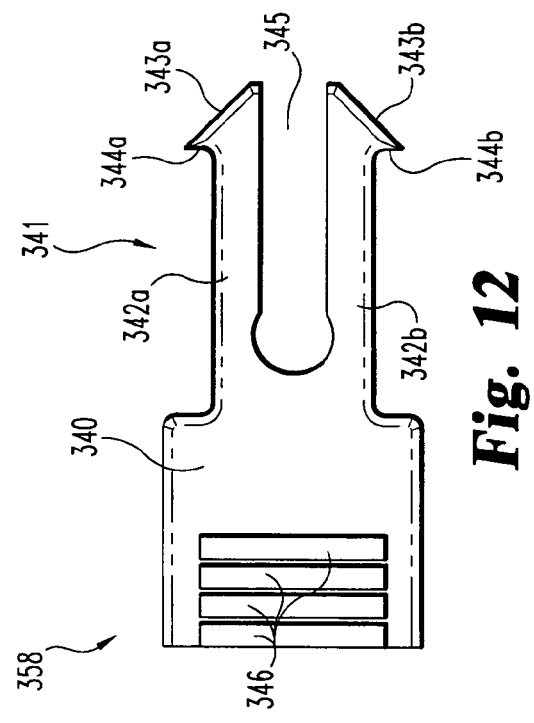
FIG. 12 is a plan view of a guide member employed with the spinal plate of FIG. 8.
Figure 13:
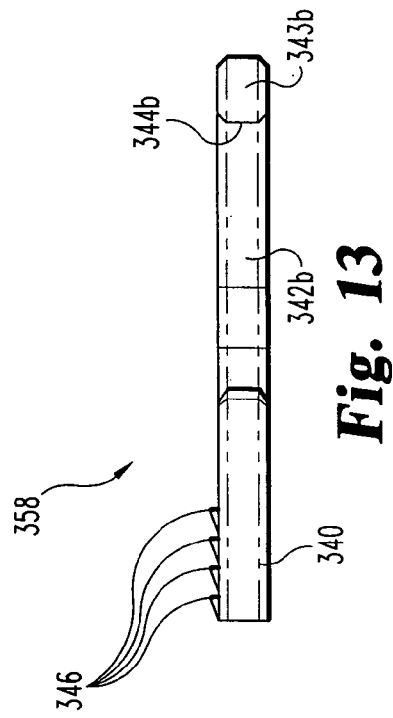
FIG. 13 is an elevational view of the retaining arm of FIG. 12.
Figure 10:
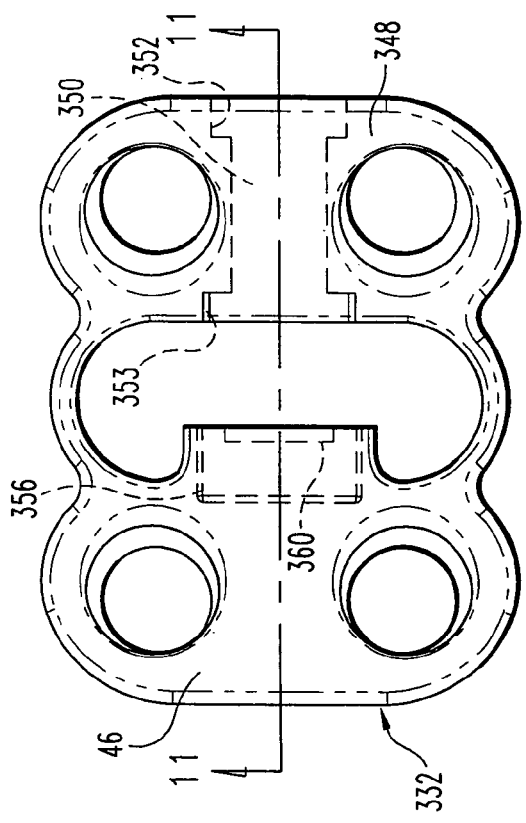
FIG. 10 is a top plan view of a plate body of the spinal plate of FIG. 8.
Figure 11:
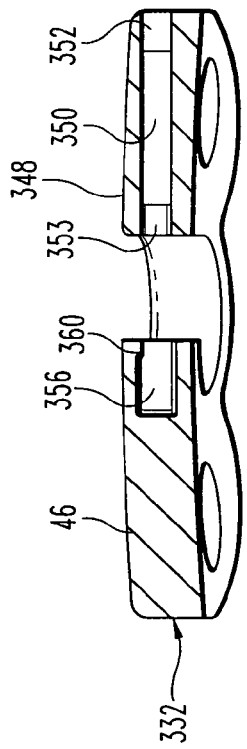
FIG. 11 is a section view along line 11-11 of FIG. 10.
Figure 17:
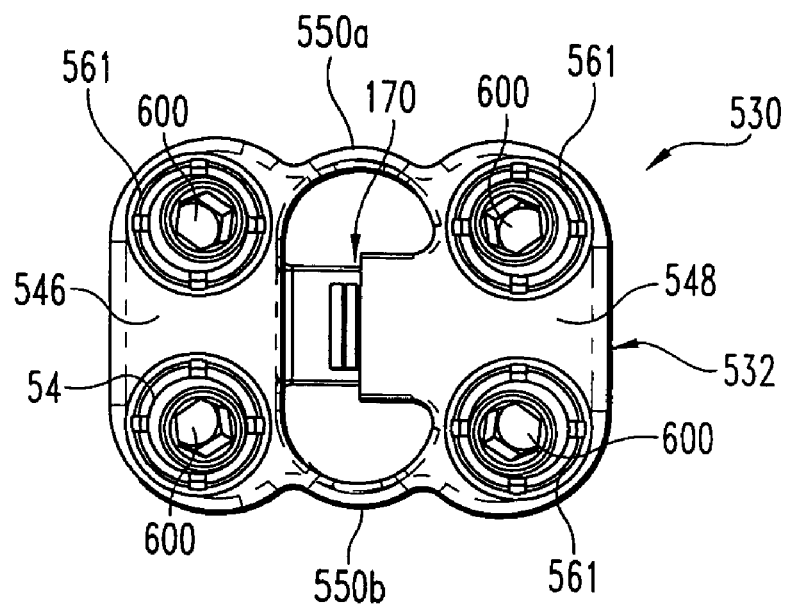
FIG. 17 is a top plan view of another embodiment spinal plate with bone anchors.

Guide member retaining passage 350 is shown with the depiction of plate body 332 in FIGS. 10-11 with guide member 358 removed. Retaining passage 350 includes a first enlarged end portion 352 adjacent one end of plate body 332 and an opposite enlarged second end portion 353 adjacent to window 54. Guide member 358, shown in isolation in FIGS. 12-13, includes a body portion 340 having a toothed surface with teeth 346 extending thereacross. Guide member 358 further includes a mounting portion 341 with first and second legs 342a, 342b extending from body portion 340 that are separated by a slot 345. The ends of legs 342a, 342b remote from body portion 340 include a respective one of the retaining flanges 344a, 344b projecting outwardly therefrom. Sloped wall surfaces 343a, 343b extend along the opposite sides of flanges 344a, 344b and taper toward one another in the direction extending away from body portion 340.

Guide member 358 can be inserted into retaining passage 350 with sloped surfaces 343a, 343b contacting the inner sides of retaining passage 350 to compress legs 342a, 342b toward one another along slot 345 to allow legs 342a, 342b to move along retaining passage 350. When flanges 344a, 344b are aligned with enlarged end portion 352 of retaining passage 350, legs 342a, 342b can spring outwardly to engage flanges 344a, 344b in enlarged end portion 352. A part of body portion 340 resides in enlarged end portion 353 of passage 350, securing guide member 358 in vertebral engaging portion 348.

As shown in FIGS. 8-9, guide member 358 extends from retaining passage 350 toward receptacle 356. Receptacle 356 includes a retaining lip 360 engageable with an adjacent one of the teeth 346 as plate body 332 is compressed under compression loading. Engagement of retaining lip 360 with the adjacent tooth 346 limits movement of the vertebral engaging portions and thus the vertebrae away from one another while allowing uni-directional translation in compression to maintain graft loading.

FIGS. 14-16 show another embodiment spinal plate 430 having a plate body 432. Body 432 is similar to body 32 discussed above, but plate 430 includes another embodiment guide assembly 470 and a vertebral engaging portion 446 that is configured to interact with the same. Vertebral engaging portion 446 includes a receptacle 456 having a number of retaining lips 460 extending thereacross. Vertebral engaging portion 446 also includes a slot 462 extending therealong transversely to and interrupting retaining lips 460 that also opens into receptacle 456.

Vertebral engaging portion 48 includes a guide member 458 extending toward and positionable in receptacle 456. Guide member 458 includes a spring 444 extending thereacross that is captured in a recess 446 formed between side rails extending along guide member 458. As shown in FIG. 16, spring 444 can flex outwardly so as to normally engage an adjacent one of the retaining lips 460 as guide member 458 is advanced into receptacle 456 in response to axial compression of plate 430. Engagement between spring 444 and the adjacent retaining lip 460 maintains the compression load on the bone graft while resisting movement of the vertebrae away from one another. If it is desired to allow vertebral engaging portions 446, 48 to move away from one another, spring 444 can be accessed through slot 462 and compressed to disengage spring 444 from the adjacent lip 460, allowing movement of vertebral engaging portions 446, 48 away from one another.

FIGS. 17-22 show another embodiment plate 530 that can be configured with a guide assembly in accordance with any of the embodiments discussed herein. In the illustrated embodiment, guide assembly 170 is shown with plate body 532. Spinal plate 530 differs from the other spinal plate embodiments in that it is shown with a retaining element adjacent each of the plate holes. However, it should be understood that any of the plate embodiments may incorporate the retaining element of FIGS. 17-22 or any other suitable device for retaining, preventing or resisting anchors from backing out of the plate holes.

Plate 530 includes a plate body 532 having a first vertebral engaging portion 546 engaged to a first vertebra V1 with anchors 600, and a second vertebral engaging portion 548 engaged to a second vertebra V2 with anchors 600. One or more implants I having bone graft and/or other suitable bone growth promoting materials can be positioned in the disc space between vertebrae V1, V2. Engaging portions 546, 548 are movable toward and away from one another in response to axial compression and tension loading of plate 530 via flexing of intermediate portions 550a, 550b extending therebetween as discussed above with respect to plate 30. In addition, guide assembly 170 can provide additional strength in resisting bending forces created by spinal flexion and extension, and can include a ratcheting feature to permit uni-directional translation in axial compression only.

Body 532 defines holes 542a, 542b in vertebral engaging portion 546 and holes 544a, 544b in vertebral engaging portion 548. Anchors 600 can be positioned in respective ones of the holes 542a, 542b, 544a, 544b to engage plate 530 to the respective vertebrae V1, V2. In addition, plate 530 includes a retaining element 561a, 561b, 561c, 561d extending about each of the respective holes 542a, 543b, 544a, 544b. As shown with respect to retaining element 561a in FIGS. 21-22, retaining element 561a includes a number of fingers 562 spaced about the perimeter of hole 542a that are adjacent the upper or proximal surface of plate 530. Fingers 562 are separated from one another by groove 563 such that four fingers 562 are provided in the illustrated embodiment. Each finger 562 includes an L shape with a vertically or proximally extending leg 565 and a horizontally extending leg 566 extending from the outer end of the respective leg 565 and radially inwardly toward hole 542a. A circumferential groove 564 in the upper plate surface extends about each of the fingers 562 along first leg 565, facilitating fingers 562 in flexing radially outwardly to permit insertion of the anchor therethrough into hole 542a. Fingers 562 can resiliently return toward their pre-anchor insertion configuration to block or prevent the anchor from backing out of plate hole 542a.

Figure 19:
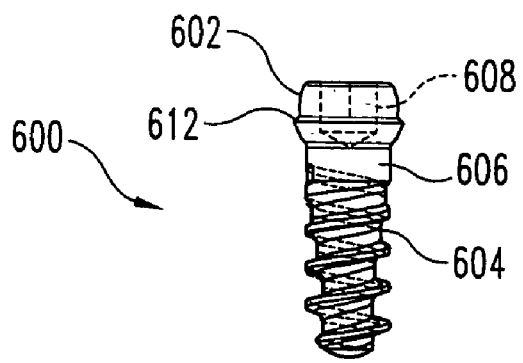
FIG. 19 is an elevational view of one of the bone anchors of FIG. 17.
Figure 18:
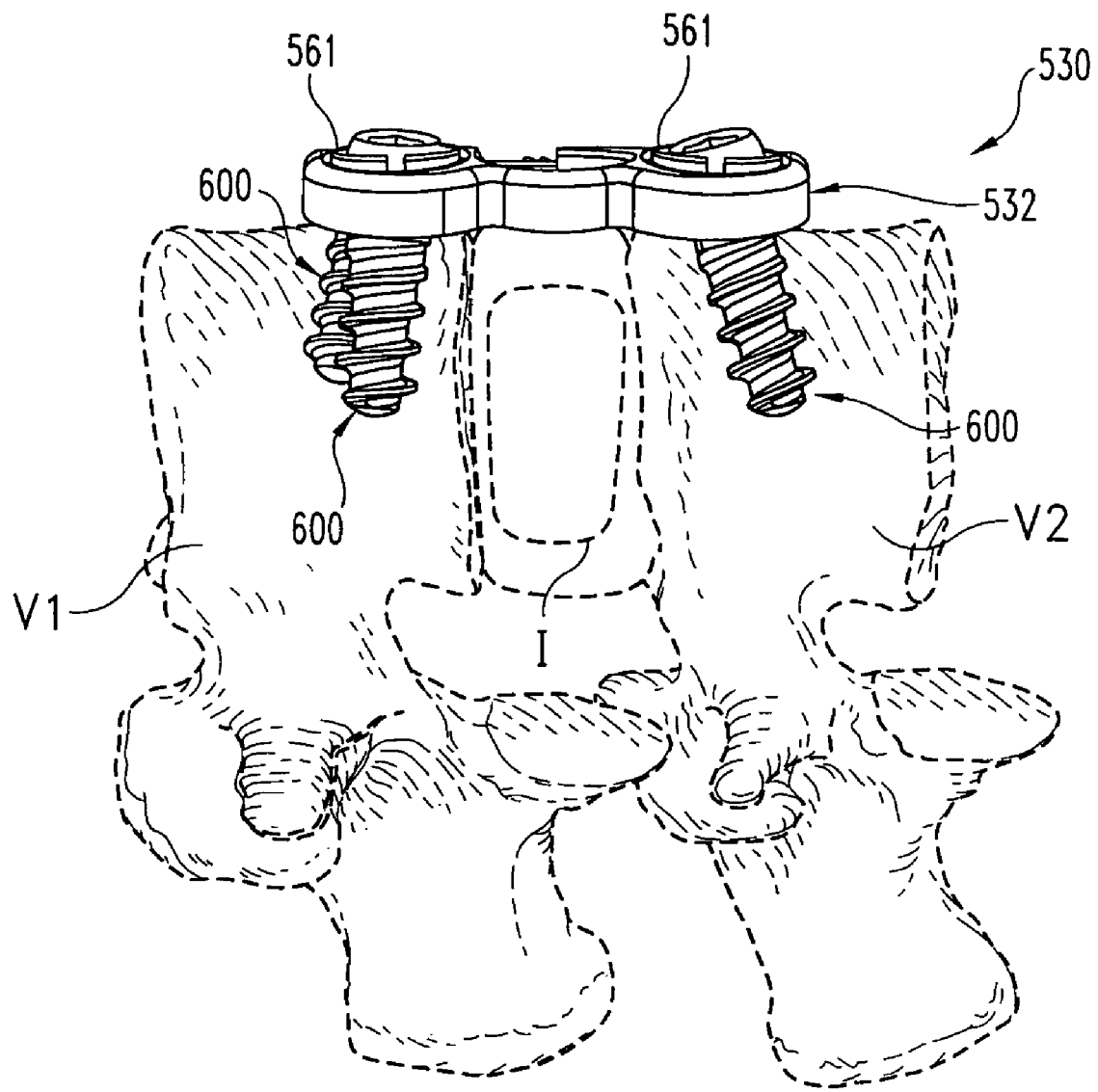
FIG. 18 is an elevational view of the spinal plate and bone anchors of FIG. 17.
Figure 20:
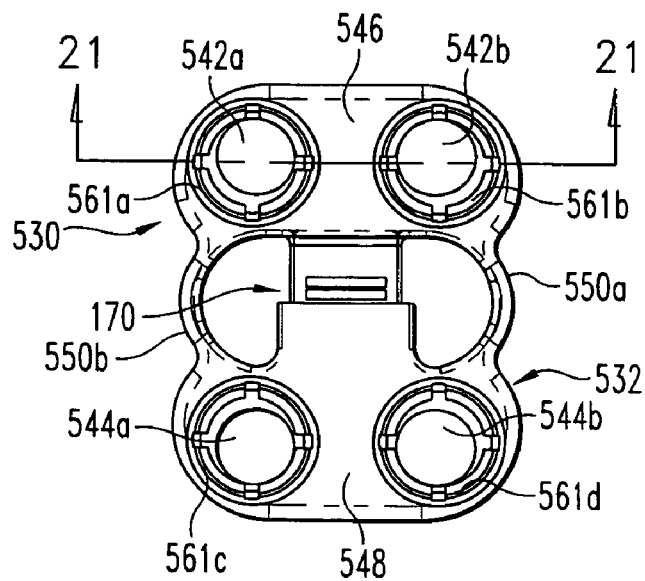
FIG. 20 is a top plan view of the spinal plate of FIG. 17.
Figure 21:
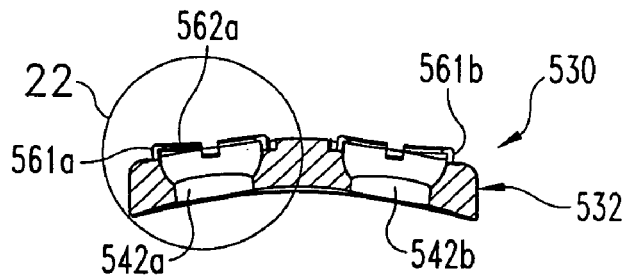
FIG. 21 is a section view along line 21-21 of FIG. 20.
Figure 22:
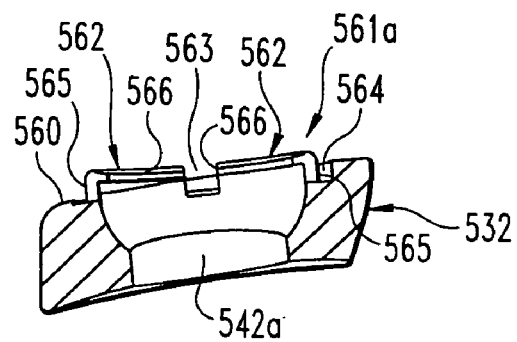
FIG. 22 is an enlarged, detailed view of the region 22 indicated in FIG. 21.

One embodiment for anchor 600 is further shown in FIG. 19. Anchor 600 includes a proximal head portion 602 having enlarged and generally spherical shape extending about a distally extending shaft portion 604. An intermediate neck portion 606 can extend between head portion 602 and shaft portion 604. Head portion 602 can include an internal tool engaging recess 608 to receive and engage a driving tool. In addition, head portion 602 can include a proximally oriented retaining flange 612 extending thereabout.

As anchor 600 is positioned through one of the plate holes 542a, 542b, 544a, 544b, retaining element 561 allows passage therethrough since fingers 562 deflect radially outwardly as head portion 602 comes into contact therewith. Once head portion 602 is driven distally beyond fingers 562, the fingers 562 can return toward their unflexed condition and engage head portion 602 proximally of or against retaining flange 612, preventing anchor 600 from backing out proximally from the plate hole. Anchor 600 provides a structure that can be positively engaged by the retaining element 561 to provide a one step locking mechanism that automatically locks the anchor in the plate hole when the anchor is inserted. Retaining elements 561 can be machined into body 532 of plate 530, molded with body 532 of plate 530, or be in the form of separate components engaged to body 532 of plate 530.

The bone plates herein may include any suitable overall shape and form for plates for spinal stabilization, including plates employed for anterior, antero-lateral, lateral, and posterior stabilization procedures. The plate holes for receiving the anchors can be generally circular in shape; however, it should be appreciated that the holes can be configured or shaped differently in any manner suitable for receipt of an anchor. For example, the holes or portions thereof can be cylindrical, partially spherical, frusto-conical, elongated, oval, slotted, and combinations thereof. Further, it should be appreciated that holes can be provided through the bone plates either in isolation, in adjacent hole pairs, or three or more adjacent holes.

The plates discussed herein can be made from any one or a combination of suitable material or materials, including metals and metal alloys, polymers, biological materials, synthetic materials, and resorbable materials, for example. In one embodiment, the body of the plate is made from a first material that facilitates the flexibility or deformability of the intermediate portions between the vertebral engaging portions, and the guide assembly is made from a second material so the components of the guide assembly are attached to or molded in the body of the plate. In one specific example, the plate body is made from PEEK material and the guide assembly is made from a metal or metal alloy such as titanium.

The anchors employed to attach the plate to the vertebrae can include a proximal head and a distal bone engaging portion. The bone engaging portion can include a thread pattern therealong to engage bony structure of the vertebral body underlying the plate hole through which the anchor is positioned. The bone engaging portion of the anchors includes an elongated shaft structure with a generally cylindrical shape, although other shapes are also contemplated, including circular, square, rectangular, polygonal shape, and any other suitable shape for passage through a plate hole and engagement with bony structure. When positioned in the plate hole, the head of the anchor can be fixed, pivotal, translatable or otherwise movable in the hole. It is contemplated that the head can extend at or at least slightly above the upper proximal surface of the plate, or could be recessed distally below the upper surface.

The use of a plating system by a surgeon may involve inserting retaining members adjacent one or more of the holes in the plate after placement of one or more anchors in the holes of the plate. The retaining members can be separate components attached to the plate after implantation of the plate, or pre-attached to the plate and moveable relative to the plate to a position that prevents the anchors from backing out of the plate holes. After implantation and securement of the bone plate to the bony structure, the retaining member prevents and/or limits the backout of one or more anchors relative to the plate. Specifically, the interference between the retaining member and the head of the anchor blocks the anchor from backing out of the plate hole and out of engagement with bony structure underlying the plate and into tissue surrounding the plate.

While the invention has been illustrated and described in detail in the drawings and foregoing description, the same is to be considered as illustrative and not restrictive in character. For example, the spinal plates can extend along three or more vertebrae with one or more flexible intermediate portions. The spinal plates can also include two or more intermediate portions to provide multiple flexing regions. The multiple flexible regions can be aligned with respective disc spaces along a multi-level stabilization procedure. All changes and modifications that come within the spirit of the invention are desired to be protected.

What is claimed is:

1. A spinal plating system, comprising:
a unitary plate body extending along a longitudinal axis between a first end and an opposite second end, said plate body having a length along said longitudinal axis sized to extend between at least a first vertebra and a second vertebra of a spinal column, wherein said plate body includes:
a first vertebral engaging portion with at least one hole extending between an upper surface and a lower surface of said plate body, said at least one hole for receiving a first anchor to secure said first vertebral engaging portion to the first vertebra;
a second vertebral engaging portion with at least one hole extending between said upper and lower surfaces of said plate body, said at least one hole for receiving a second anchor to secure said second vertebral engaging portion to the second vertebra;
first and second intermediate portions extending between said first and second vertebral engaging portions along opposite sides of said plate body, said first and second intermediate portions and said first and second vertebral engaging portions defining a window therebetween, wherein said first and second intermediate portions are sized and structured to flex outwardly away from said longitudinal axis and permit said first and second vertebral engaging portions to move toward one another along said longitudinal axis in response to compression loading of said plate body along said longitudinal axis, wherein said first and second intermediate portions have a convex arcuate shape in relation to said longitudinal axis; and
a guide assembly in said window along said longitudinal axis extending between and engaged to said first and second vertebral engaging portions, said guide assembly including a guide member movably received in a receptacle as said first and second vertebral engaging portions move toward one another, wherein said guide assembly includes a temporary locking mechanism configured to temporarily secure said guide member in a respective position in said receptacle as said first and second vertebral engaging portions move toward one another while inhibiting said first and second vertebral engaging portions from moving away from one another.

2. The system of claim 1, wherein when said plate body is uncompressed along said longitudinal axis said guide member is positioned outside said receptacle and when said plate body is compressed along said longitudinal axis to move said vertebral engaging portions toward one another said guide member is received in said receptacle.

3. The system of claim 1, wherein said receptacle includes a retaining lip and said guide member includes a retaining member engageable with said retaining lip when said guide member is positioned in said receptacle to inhibit movement of said first and second vertebral engaging portions away from one another.

4. The system of claim 3, wherein said retaining member comprises a spring.

5. The system of claim 4, wherein said spring is positioned in a recessed portion of said guide member such that a portion of said spring protrudes upwardly from an upper surface of said guide member.

6. The system of claim 4, wherein said spring includes a sloped portion such that said spring may slide into said receptacle.

7. The system of claim 4, wherein said spring includes a sloped portion and an engaging portion, wherein said sloped portion allows said spring to compress such that said guide member can be received in said receptacle and said engaging portion is configured to limit movement of said first and second vertebral engaging portions away from one another.

8. The system of claim 3, wherein said receptacle includes a slot and at least a portion of said retaining member is exposed in said slot such that upon application of force to said retaining member through said slot said first and second vertebral engaging portions are permitted to move away from one another.

9. The system of claim 1, wherein said temporary locking mechanism comprises a number of teeth extending across said receptacle and a spring protruding upwardly from an upper surface of said guide member engageable with an adjacent one of said teeth when said guide member is received in said receptacle, said engagement between said spring and said teeth limiting movement of said vertebral engaging portions away from one another.

10. A spinal plating system, comprising:
a unitary plate body extending along a longitudinal axis between a first end and an opposite second end, said plate body having a length along said longitudinal axis sized to extend between at least a first vertebra and a second vertebra of a spinal column, wherein said plate body includes a first vertebral engaging portion and a second vertebral engaging portion opposite said first vertebral engaging portion, a first and second intermediate portion extending between said first and second vertebral engaging portions along opposite sides of said plate body, said first and second intermediate portions and said first and second vertebral engaging portions defining a window therebetween, wherein said first and second intermediate portions are configured to flex outwardly away from said longitudinal axis thereby permitting said first and second vertebral engaging portions to move toward one another along said longitudinal axis in response to compression loading of said plate body along said longitudinal axis; and
wherein said first vertebral engaging portion includes a receptacle extending into said window and said second vertebral engaging portion includes a guide member extending toward said receptacle sized and configured to be movably received in said receptacle, wherein said receptacle includes means for receiving a spring protruding from an upper surface of said guide member such that said first and second vertebral engaging portions are limited from moving away from one another.

11. The system of claim 10, wherein said means for receiving comprises a plurality of retaining lips positioned on an upper inner surface of said receptacle.

12. The system of claim 11, wherein said retaining lips include a sloped portion and a generally vertical portion, wherein a portion of said spring is configured to engage said generally vertical portion to limit said first and second vertebral engaging portions from moving away from one another.

13. The system of claim 10, wherein said spring includes a sloped front portion and a generally vertical back portion, wherein said sloped front portion allows said second vertebral engaging portion to move toward said first vertebral engaging portion while positioned in said means for receiving said spring and said generally vertical back portion prevents said first and second vertebral engaging portions from moving away from one another while positioned in said means for receiving said spring.

14. The system of claim 10, wherein said receptacle and said guide member are sized and configured to prevent lateral movement of said first and second vertebral engaging portions.

15. A spinal plating system, comprising:
a unitary plate body extending along a longitudinal axis between a first end and an opposite second end, wherein said plate body includes a first vertebral engaging portion and a second vertebral engaging portion, said plate body further including a first and second intermediate portion extending between said first and second vertebral engaging portions along opposite sides of said plate body defining a window therebetween that permit said first and second vertebral engaging portions to move toward one another along said longitudinal axis, wherein said first and second intermediate portions are configured to flex outwardly away from said longitudinal axis as said fist and second vertebral engaging portions move toward one another along said longitudinal axis; and
a guide assembly including a receptacle sized and configured to receive a guide member having a spring, wherein said spring inhibits said first and second vertebral engaging portions from moving away from one another along said longitudinal axis when said guide member is positioned in said receptacle and yet does not inhibit said first and second vertebral engaging portions from moving toward one another along said longitudinal axis.

16. The spinal plating system of claim 15, wherein said receptacle includes a plurality of retaining lips on an inner surface of said receptacle configured to receive at least a portion of said spring that is sized and configured to inhibit said first and second vertebral engaging portions from moving away from one another along said longitudinal axis.

17. The spinal plating system of claim 16, wherein said retaining lips include a first front sloped portion and a first generally vertical back portion, wherein at least a portion of said spring includes a second front sloped portion and a second generally vertical back portion, and wherein as said second vertebral engaging portion moves toward said first vertebral engaging portion said second sloped portion of said spring travels down said first sloped portion of a respective retaining lip thereby compressing said spring and when an end of said second sloped portion of said spring reaches a respective first generally vertical back portion of another retaining lip said spring decompresses somewhat thereby positioning said spring in said other retaining lip thereby inhibiting said first and second vertebral engaging portions from moving away from one another along said longitudinal axis.

18. The system of claim 15, further comprising an opening in a surface of said receptacle that is sized and oriented to expose at least a portion of an upper surface of said spring.

19. The system of claim 18, wherein said opening allows access to said spring so that said spring may be compressed to allow said first and second vertebral engaging portions to move away from one another along said longitudinal axis.

20. The system of claim 15, wherein said receptacle and said guide member are sized and configured to prevent lateral movement of said first and second vertebral engaging portions.

* * * * *